United States Patent
Ekman et al.

(10) Patent No.: US 9,295,785 B2
(45) Date of Patent: Mar. 29, 2016

(54) FRONT END FOR AN AUTO-INJECTOR

(75) Inventors: Matthew Ekman, Cheshire (GB);
Thomas Kemp, Hertfordshire (GB);
Douglas A. Jennings, Herts (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 13/996,044

(22) PCT Filed: Dec. 21, 2011

(86) PCT No.: PCT/EP2011/073516
§ 371 (c)(1),
(2), (4) Date: Jun. 20, 2013

(87) PCT Pub. No.: WO2012/085034
PCT Pub. Date: Jun. 28, 2012

(65) Prior Publication Data
US 2013/0281938 A1 Oct. 24, 2013

(30) Foreign Application Priority Data

Dec. 21, 2010 (EP) .................................... 10196080

(51) Int. Cl.
*A61M 5/32* (2006.01)
*A61M 5/50* (2006.01)
(Continued)

(52) U.S. Cl.
CPC ............... *A61M 5/3213* (2013.01); *A61M 5/20* (2013.01); *A61M 5/283* (2013.01); *A61M 5/50* (2013.01);
(Continued)

(58) Field of Classification Search
CPC . A61M 5/322; A61M 5/3234; A61M 5/5086; A61M 5/3134; A61M 5/3271; A61M 5/3243; A61M 2005/2073; A61M 5/3205; A61M 2005/3206; A61M 2005/3208; A61M 2005/3253; A61M 5/283; A61M 2005/3245; A61M 2005/3252; A61M 5/14546
USPC .................................. 604/240–243, 198, 263
See application file for complete search history.

(56) References Cited

U.S. PATENT DOCUMENTS

2002/0095120 A1 7/2002 Larsen et al.
2003/0196928 A1* 10/2003 Parsons ................... A61M 5/30
206/538

(Continued)

FOREIGN PATENT DOCUMENTS

EP 0518416 A1 12/1992
EP 2201975 A1 6/2010
(Continued)

*Primary Examiner* — Emily Schmidt
*Assistant Examiner* — William Frehe
(74) *Attorney, Agent, or Firm* — Fish & Richardson P.C.

(57) ABSTRACT

The invention relates to a front end for an auto-injector, the front end comprising a syringe with an injection needle and a stopper, wherein the syringe is slidably arranged within a syringe retainer, wherein an outer sleeve for preventing access to the needle is removably arrangeable over the syringe retainer, wherein the syringe retainer comprises a screw thread for connecting it to a correspondent screw thread of a mounting of a re-usable auto-injector back end comprising a drive means for advancing the syringe and needle in a proximal direction for needle insertion and for advancing the stopper within the syringe for injection, wherein a resilient locking barb is arranged to rotationally lock the syringe retainer to the mounting in an unscrewing direction when the front end is screwed to the re-usable back end and when the outer sleeve is removed, wherein the outer sleeve is arranged to unlock the resilient locking barb when arranged over the syringe retainer.

20 Claims, 17 Drawing Sheets

(51) Int. Cl.
*A61M 5/20* (2006.01)
*A61M 5/28* (2006.01)
*A61M 5/315* (2006.01)

(52) U.S. Cl.
CPC .......... *A61M 5/31571* (2013.01); *A61M 5/3202* (2013.01); *A61M 2005/206* (2013.01); *A61M 2005/2013* (2013.01); *A61M 2205/273* (2013.01); *A61M 2205/276* (2013.01)

(56) References Cited

U.S. PATENT DOCUMENTS

| | | | |
|---|---|---|---|
| 2008/0228147 A1* | 9/2008 | David-Hegerich et al. ... | 604/198 |
| 2009/0227955 A1* | 9/2009 | Hirschel ............ | A61M 5/2448 604/187 |
| 2010/0016793 A1* | 1/2010 | Jennings et al. .............. | 604/134 |
| 2013/0274655 A1* | 10/2013 | Jennings ................ | A61M 5/20 604/67 |
| 2013/0274671 A1* | 10/2013 | Jennings ................ | A61M 5/20 604/154 |
| 2013/0274677 A1* | 10/2013 | Ekman .................... | A61M 5/20 604/197 |

FOREIGN PATENT DOCUMENTS

| | | | | |
|---|---|---|---|---|
| GB | 2445090 A | | 6/2008 | |
| WO | 0009186 A2 | | 2/2000 | |
| WO | WO2010023481 | * | 3/2010 | .................... 604/192 |
| WO | WO 2010023481 A1 | * | 3/2010 | .......... A61M 5/2033 |
| WO | WO2010076569 | * | 7/2010 | .................... 604/198 |

* cited by examiner

FRONT END FOR AN AUTO-INJECTOR

CROSS REFERENCE TO RELATED APPLICATIONS

The present application is a U.S. National Phase Application pursuant to 35 U.S.C. §371 of International Application No. PCT/EP2011/073516 filed Dec. 21, 2011, which claims priority to European Patent Application No. 10196080.5 filed Dec. 21, 2010. The entire disclosure contents of these applications are herewith incorporated by reference into the present application.

FIELD OF INVENTION

The invention relates to a front end for an auto-injector according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an under dose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

Most conventional art auto-injectors are disposable, i.e. they are used and completely disposed of after use. For reasons of sustainability it may be desirable to re-use at least a part of the auto-injector. An auto-injector may therefore consist of a re-usable back end engine containing drive means and a front end containing the syringe with the needle which must not be re-used.

SUMMARY

It is an object of the present invention to provide an improved front end for an auto-injector.

The object is achieved by a front end according to claim 1.

Preferred embodiments of the invention are given in the dependent claims.

In the context of this specification the term proximal refers to the direction pointing towards the patient during an injection while the term distal refers to the opposite direction pointing away from the patient.

A front end for an auto-injector according to the invention comprises a syringe with an injection needle and a stopper. The syringe is slidably arranged within a syringe retainer. An outer sleeve or cap for preventing pre and post injection access to the needle is removably arrangeable over the syringe and syringe retainer. The syringe retainer comprises a screw thread for connecting it to a correspondent screw thread of a mounting of a re-usable auto-injector back end, the back end comprising a drive means for advancing the syringe and needle in a proximal direction for needle insertion and for advancing the stopper within the syringe for injection. A resilient locking barb is arranged to rotationally lock the syringe retainer to the mounting in an unscrewing direction of rotation when the front end is screwed to the re-usable back end and when the outer sleeve is removed. The outer sleeve is arranged to unlock the resilient locking barb when arranged over the syringe retainer. This avoids removal of the front end from the back end without the outer sleeve or cap being reapplied to the front end thus reducing the risk of post injection needle stick injuries.

The invention provides a means to ensure fitment of the correct syringe to the back end. This may help to ensure that the intended drug is used with the re-usable auto-injector.

The locking barb may be arranged on the syringe retainer proximally from the screw thread. The locking barb is arranged to engage an internal groove arranged in the mounting for locking the syringe retainer to the mounting. The locking barb is arranged to partially remain outside of the mounting when the syringe retainer is fully screwed to the mounting so as to allow the outer sleeve to engage it and to inwardly deflect the locking barb to unlock it so that the syringe retainer can be unscrewed from the mounting.

The locking barb may exhibit a chamfer for inwardly deflecting the locking barb by an internal surface of the mounting when rotated in a screwing direction. This allows for screwing the front end to the mounting even if the outer sleeve or cap is already removed.

If a protective needle sheath on the needle is intended to be pulled off the needle on removal of the outer sleeve the syringe has to be prevented from translating out of the distal position. A syringe lock may be arranged for preventing translation of the syringe from a distal position in the proximal direction when the outer sleeve is arranged over the syringe retainer. This ensures that the syringe remains in the distal position.

The syringe may be arranged in a tubular syringe carrier arranged to support the syringe at its proximal end. This is preferred over holding the syringe at a finger flange since a neck at the proximal end of the syringe is less prone to break when subjected to impact load. The syringe carrier is slidably arranged in the syringe retainer.

The syringe lock may comprise a hub extending through a lateral aperture in the syringe retainer in a manner to engage the finger flange of the syringe or a second shoulder on a distal end of the syringe carrier. The hub is outwardly biased, e.g. by a spring or resilient arms on the hub so as to disengage the finger flange or second shoulder in a manner to allow translation in the proximal direction. The outer sleeve is arranged to outwardly support the hub when attached to the syringe retainer so as to prevent outward deflection and disengagement of the syringe lock.

A syringe spring may be arranged to bias the syringe in the distal direction. This allows for a defined position of the syringe prior to needle insertion. The syringe may be advanced against the load of the syringe spring by a plunger of the re-usable back end pushing on the stopper for needle insertion. After injection, the plunger may be retracted by the back-end allowing the syringe spring to retract the syringe and needle for providing post-injection needle safety.

The syringe may be arranged within an elongate housing telescoped within the syringe retainer. The housing may be biased in the proximal direction and arranged to be translated in the distal direction when applied against an injection site thus serving as a transfer sleeve indicating skin contact. A distal end of the housing is arranged to protrude towards the re-usable back end to indicate its longitudinal position to the re-usable back end. The re-usable back end may have a mechanical means or an electrical or optical sensor engaged to the distal end of the housing. An injection would preferably only be triggered when the housing has been translated indicating skin contact thus enforcing a sequence of operation and increasing pre injection needle safety.

A cover retainer may be arranged in the outer sleeve extending distally and inwardly at an angle, wherein the cover retainer is inwardly biased so as to engage an outward surface of the housing in an initial state and during removal of the outer sleeve. The cover retainer is arranged to deflect inwards when having travelled beyond a proximal end of the housing such that the cover retainer cannot re-enter the space between the housing and outer sleeve when the outer sleeve is reapplied to the housing. Instead the cover retainer hits the proximal end of the housing and is deformed on re-application resulting in a shape opposing removal of the outer sleeve after reapplication. This reduces the risk of a user tampering with the front end post injection and after removal from the re-usable back end.

At least one transfer spring may be arranged as a resilient part integrally moulded with the housing for biasing the housing in the proximal direction against the syringe retainer.

The protective needle sheath may be removably arrangeable over the needle. The protective needle sheath may be attached to the outer sleeve so as to be removed from the needle on removal of the outer sleeve from the syringe retainer.

For this purpose the outer sleeve may be attached to the protective needle sheath by a push fit or bump or snap fit or glued or ultrasonic welded.

In another embodiment a star washer may be arranged over an external diameter of the protective needle sheath and outwardly engaged to an internal diameter of the outer sleeve so as to couple the protective needle sheath to the outer sleeve for joint axial translation.

In yet another embodiment the protective needle sheath may have an external profiled structure in the shape of a finger grip, wherein the outer sleeve has at least one profiled arm extending in the distal direction from the proximal end face of the outer sleeve. The profiled arm is engaged to the profiled structure of the protective needle sheath. The housing is arranged to outwardly support the profiled arm when the outer sleeve is attached to the syringe retainer such that the profiled arm is prevented from deflecting outwards.

In yet another embodiment the outer sleeve may have at least one distal snap engaged distally behind a distal edge or shoulder of the protective needle sheath.

The syringe may be arranged in the front end in a manner to prevent its removal after injection. Such an arrangement may be referred to as a packaged syringe which has to be entirely disposed of after use. This embodiment ensures that contact with the user, in an area immediately surrounding the injection site, is limited to the single-use packaged syringe. This may help to prevent cross contamination between consecutive injections and may eliminate the requirement for cleaning re-usable elements. Re-use of an emptied syringe is prevented. This reduces the chance of the user being subjected to the health risks associated.

In another embodiment the syringe may be replaceably arranged in the front end.

The re-usable back end may comprise a conventional spring, a gas spring, an electric motor or another drive means for advancing the syringe and the stopper.

The front end may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
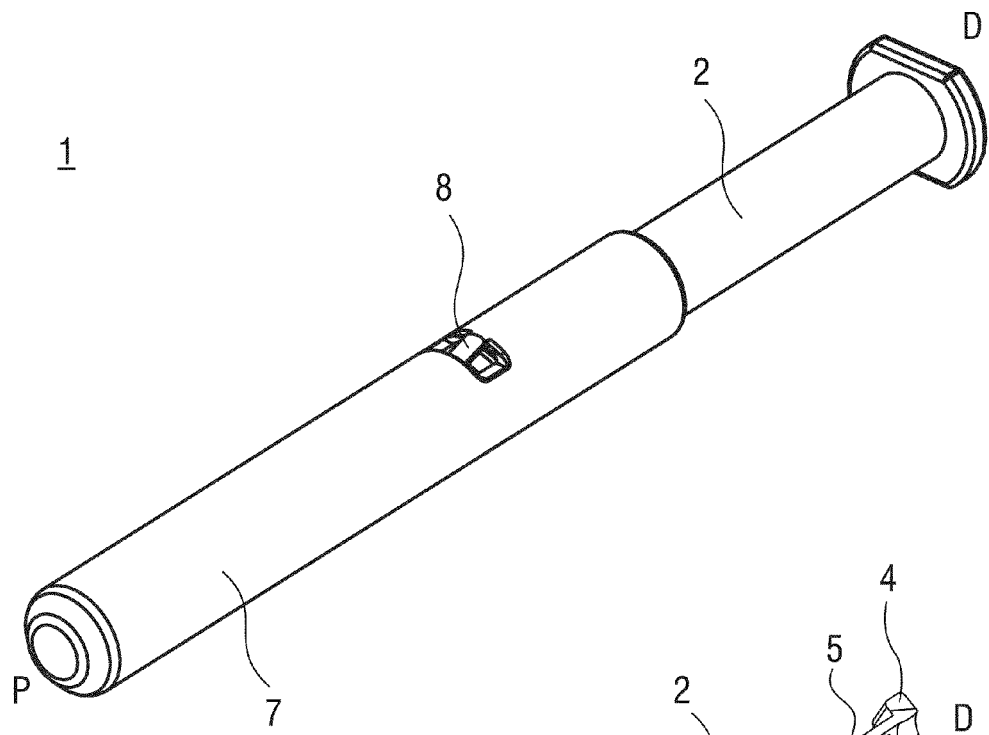
FIG. 1 is an isometric view of a first embodiment of a front end.
Figure 2:
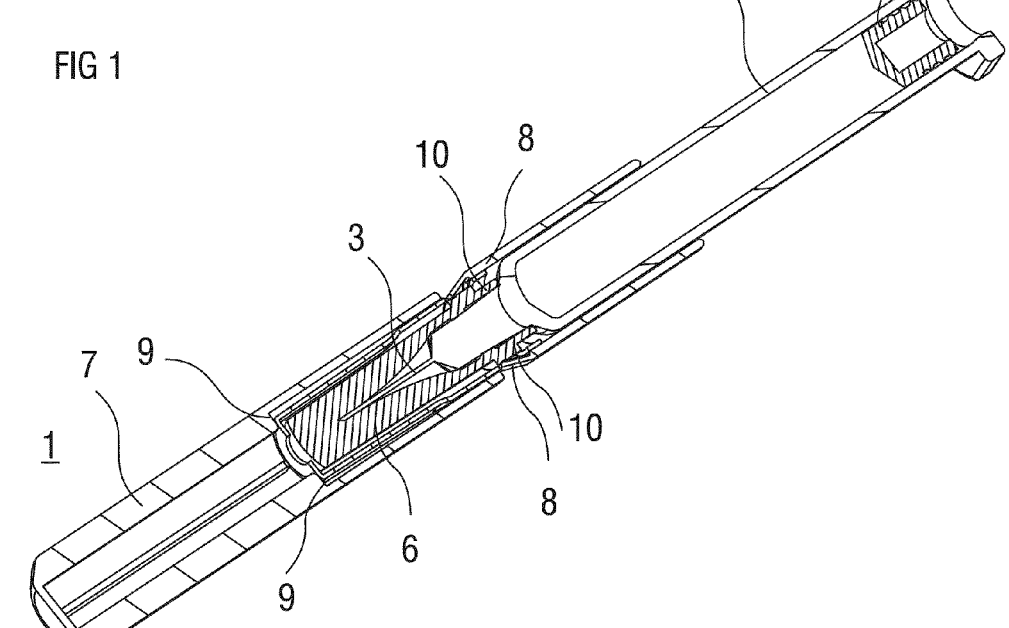
FIG. 2 is an isometric longitudinal section of the first embodiment.

FIG. 1 is an isometric view of a first embodiment of a front end 1 intended to be attached to a re-usable engine back end of an auto-injector (not illustrated). FIG. 2 is a respective longitudinal section of the front end 1.

The front end 1 comprises a syringe 2 with an injection needle 3 attached to a proximal end of the syringe 2. At a distal end the syringe 2 comprises a finger flange 4. A stopper 5 is slidably arranged in the syringe 2 for distally sealing a cavity in the syringe 2 arranged to contain a liquid medicament M. The stopper 5 may be translated in a proximal direction P within the syringe in order to displace the medicament M through the needle 3. A protective needle sheath 6 is removably arranged over the needle 3 for protecting the needle 3 from mechanical damage and for preventing finger access to the needle 3 thus reducing the risk of needle stick injuries.

An outer sleeve 7 is removably arranged over at least part of the length of the syringe 2 thereby entirely covering the protective needle sheath 6. A substantial length of the outer sleeve 7 extends proximally beyond the protective needle sheath 6.

The outer sleeve 7 or cap may be applied to the syringe 2 prior to injection, in particular post filling. The cap may likewise be assembled prior to filling. As the outer sleeve 7 is pushed onto the syringe 2, inwardly biased resilient first barbs 8 in the outer sleeve 7 deflect outwards. First ribs 9 within the outer sleeve 7 arranged to abut against a proximal end of the protective needle sheath 6 determine a maximum depth by which the outer sleeve 7 can be applied. Once the outer sleeve 7 has reached the maximum depth, the first barbs 8 engage on a first shoulder 10 of the protective needle sheath 6 in a manner to prevent removal of the outer sleeve 7 from the protective needle sheath 6.

In order to prepare for an injection the front end 1 is loaded into the re-usable back end (not illustrated). The outer sleeve 7 is removed by being pulled in the proximal direction P thereby also removing the protective needle sheath 6.

Optionally the outer sleeve 7 and the protective needle sheath 6 may be combined as one component.

The front end 1 according to the first embodiment may facilitate loading into the re-usable back end without prior removal of the protective needle sheath 6. This may reduce the chance of the user incurring an injury when loading the syringe 2.

If the protective needle sheath 6 is removed once loaded in the re-usable back end, the outer sleeve 7 being considerably longer than the protective needle sheath 6 may be used to improve access to the protective needle sheath 6. For this purpose the outer sleeve 7 may protrude through a proximal opening in the re-usable back end. This may enable the re-usable back end to be configured with the syringe 2 recessed within the back end. This should ensure that the user cannot access the needle 3 and thus improve needle safety.

The front end 1 may be assembled into the re-usable back-end by loading it from the distal direction D.

Figure 3:
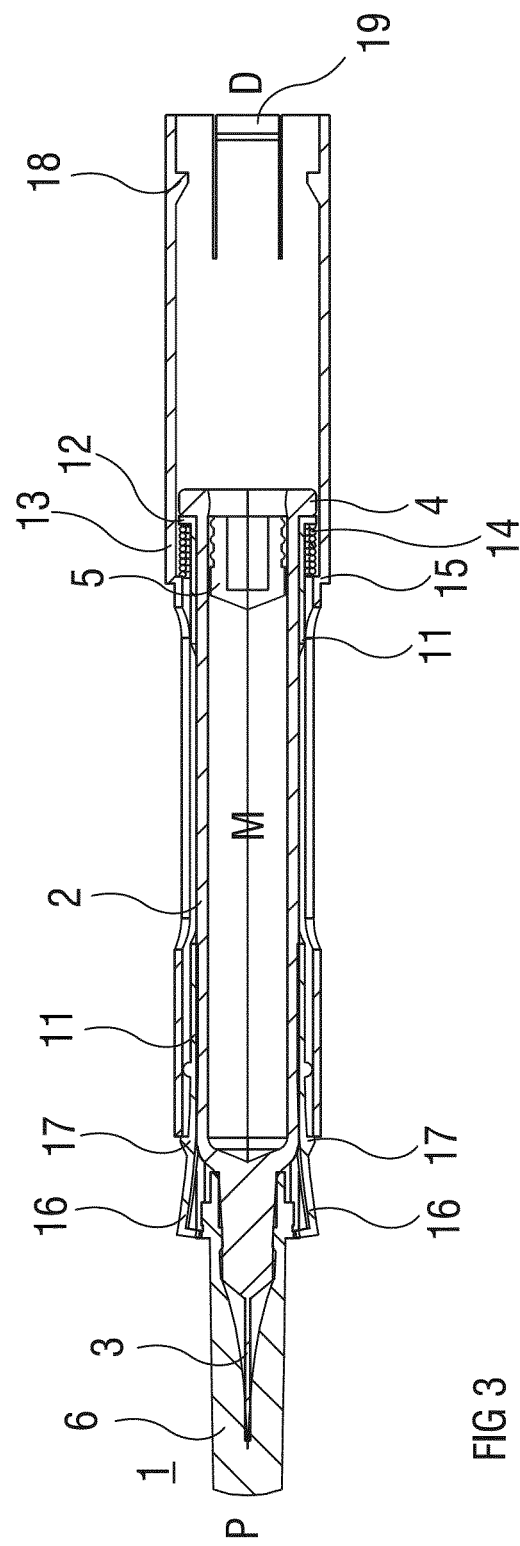
FIG. 3 is a longitudinal section of a second embodiment of the front end.

FIG. 3 is a longitudinal section of a second embodiment of the front end 1 prior to use.

The front end 1 comprises a syringe 2 with an injection needle 3 attached to a proximal end of the syringe 2. At a distal end the syringe 2 comprises a finger flange 4. A stopper 5 is slidably arranged in the syringe 2 for distally sealing a cavity in the syringe 2 arranged to contain a liquid medicament M. The stopper 5 may be translated in a proximal direction P within the syringe in order to displace the medicament M through the needle 3. A protective needle sheath 6 is removably arranged over the needle 3 for protecting the needle 3 from mechanical damage and for preventing finger access to the needle 3 thus reducing the risk of needle stick injuries.

The syringe 2 is arranged within a syringe carrier 11, wherein the finger flange 4 proximally abuts against a second shoulder 12 on the distal end of the syringe carrier 11 so as to couple the syringe 2 to the syringe carrier 11 for joint translation in the proximal direction P. The syringe carrier 11 is slidably arranged within an elongate housing 13. A syringe spring 14 in the shape of a compression spring is arranged between the second shoulder 12 and a third shoulder 15 in the housing 13 so as to bias the syringe carrier 11 in the distal direction with respect to the housing 13.

The syringe 2 can be assembled into the housing 13 post filling and application of the protective needle sheath 6 over the needle 3.

The front end 1 is shipped with the syringe spring 14 compressed, i.e. with the syringe carrier 11 and syringe 2 in a maximum proximal position. The force from the syringe spring 14 is resolved through resilient latch arms 16 on the proximal end of the syringe carrier 11 which are latched on to the housing 13. The latch arms 16 are outwardly deflected by the protective needle sheath 6 in a manner to engage a respective outward protrusion 17 on the latch arm 16 to the housing 13 in a manner to prevent translation of the syringe carrier 11 in the distal direction D. The syringe 2 may be prevented from moving in the distal direction D in this stage by friction between the syringe 2 and syringe carrier 11.

Figure 4:
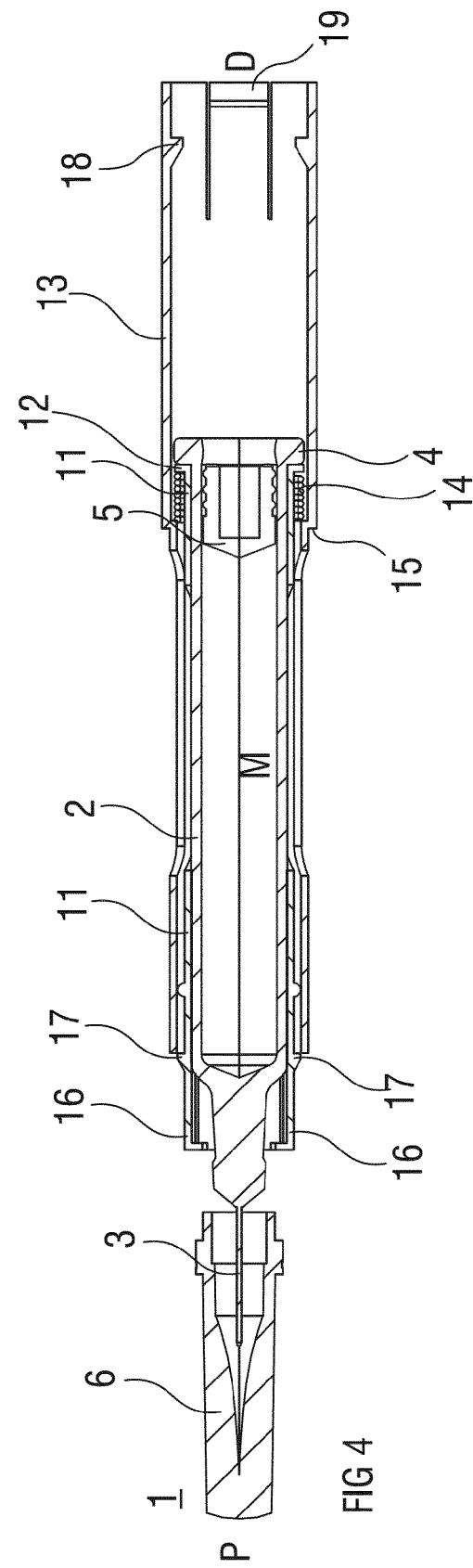
FIG. 4 is a longitudinal section of the second embodiment upon removal of a protective needle sheath.

FIG. 4 is a longitudinal section of the second embodiment of the front end 1 upon removal of the protective needle sheath 6.

The user removes the protective needle sheath 6 from the syringe 2 by pulling it off in the proximal direction P. Thus the latch arms 16 may deflect inwards and close in around the needle tip thereby disengaging the outward protrusions 17 from the housing 13 thus allowing translation of the syringe carrier 11 in the distal direction D. The outward protrusions 17 may have a ramp on their distal face, to pull the latch arms 16 inwards under the action of the syringe spring 14. The compressed syringe spring 14 causes the syringe carrier 11 to recede in the distal direction D entirely retracting the needle 3 within the housing 13 and protecting the user from accidental needle stick (see FIG. 5). The syringe 2 is locked within the housing 13 by resilient first snaps 18 within the housing 13 latching to the second shoulder 12 on the syringe carrier 11 respectively. The first snaps 18 exhibit a proximal ramp allowing the syringe carrier 11 to deflect the first snaps 18 outwards as it is translated in the distal direction D. A distal side of the first snaps 18 is essentially perpendicular to a longitudinal axis of the front end 1 preventing the syringe carrier 11 from re-translating in the proximal direction P as soon as the first snaps 18 flex inwards behind the syringe carrier 11. The protective needle sheath 6 may be discarded after removal.

Figure 5:
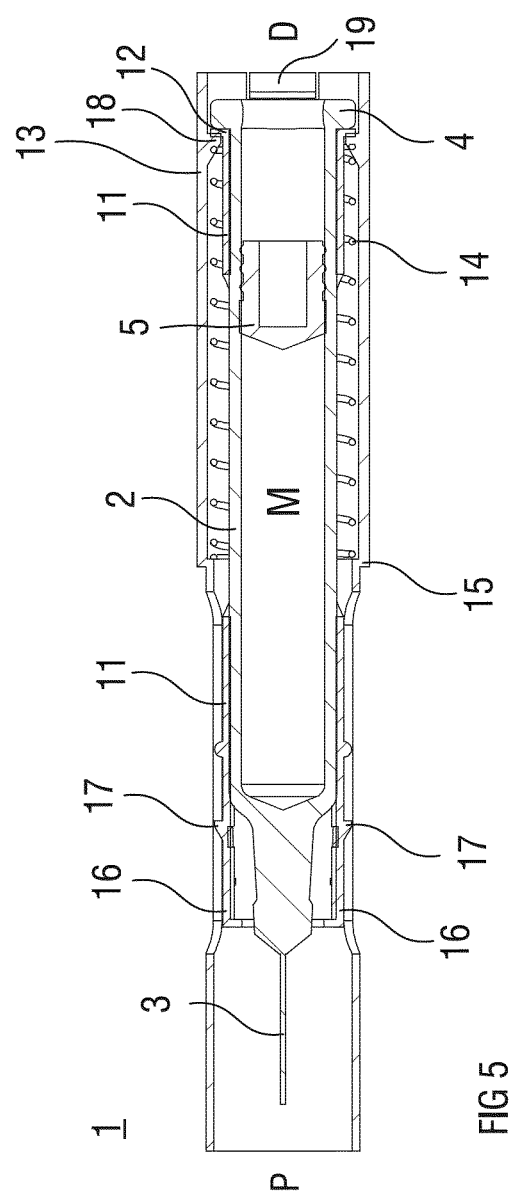
FIG. 5 is a longitudinal section of the second embodiment with a syringe retracted after removal of the protective needle sheath.
Figure 6:
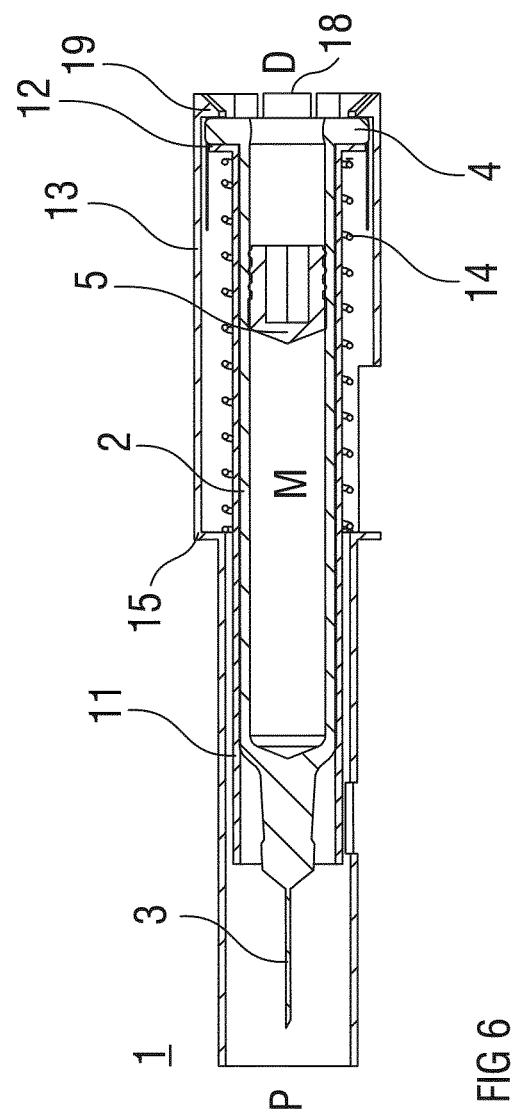
FIG. 6 is a longitudinal section of the second embodiment in a different section plane in the situation as in FIG. 5.

FIG. 6 is a longitudinal section of the second embodiment in a different section plane approximately 90° rotated relative to the section planes in FIGS. 3 to 5 in the situation as in FIG. 5. A pair of resilient second snaps 19 is arranged in the housing 13 in a manner to prevent the syringe 2 from being translated out of the distal end of the housing 13. The second snaps 19 are distally ramped to allow insertion of the syringe 2 into the housing 13 during assembly.

In order to prepare for an injection the front end 1 is connected to the re-usable back end (not illustrated). The re-usable back end is arranged to deflect the first snaps 18 outwards in a manner to de-latch them and allow translation of the syringe carrier 11 and syringe 2 in the proximal direction P. A plunger in the re-usable back end may then push on the stopper 5 and translate the syringe 2 and needle 3 in the proximal direction P into the position as in FIG. 4. In this position the syringe 2 cannot translate further. Hence the stopper 5 is translated in the proximal direction P within the syringe 2 injecting the dose of medicament into the injection site, e.g. a patient's skin. At the end of injection when the stopper 5 has bottomed out in the syringe 2 the plunger may be retracted thus allowing the syringe spring 14 to retract the syringe 2 and needle 3 in the distal direction D into a needle safe position as in FIGS. 5 and 6.

The front end 1 may be combined with the re-useable back end pre or post
removal of the protective needle sheath 6.

The front end 1 according to the second embodiment ensures the access to the needle 3 is prevented once the protective needle sheath 6 is removed. This would reduce the chance of the user incurring an injury. The housing 13 serving as a needle shroud is locked in position post injection and after removal of the front end from the back end such that needle access can only be gained through abuse of the assembly.

Figure 7:
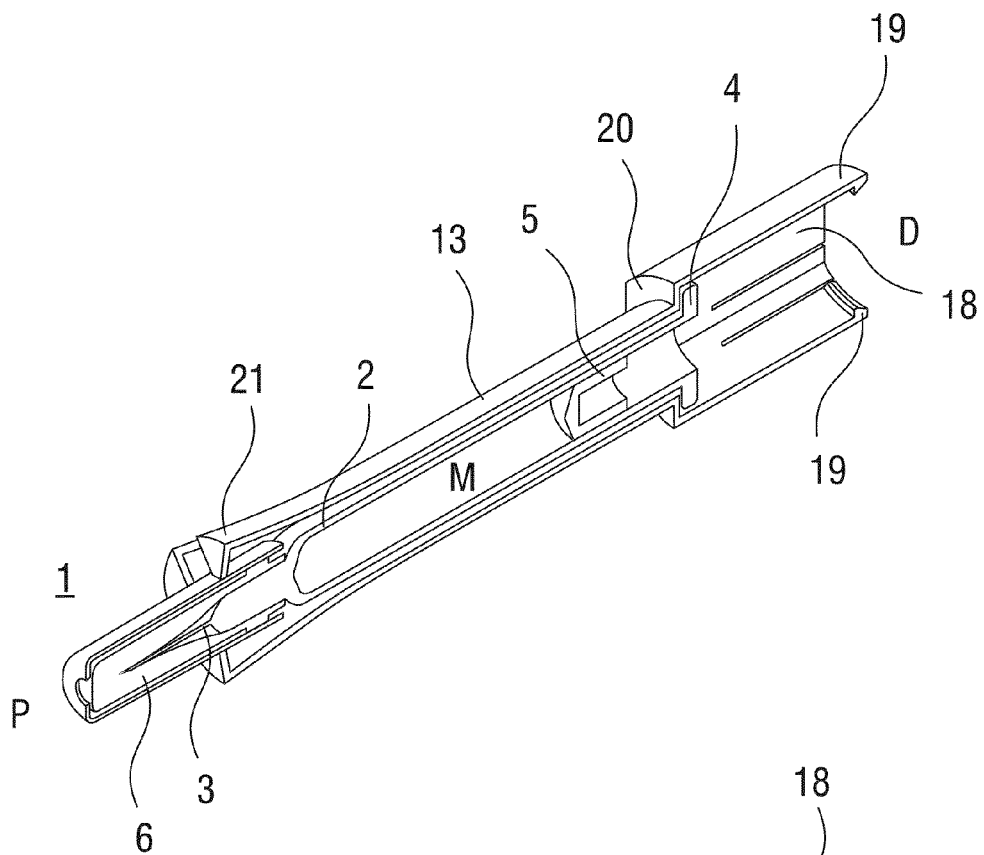
FIG. 7 is an isometric longitudinal section of a third embodiment of the front end prior to use.
Figure 8:
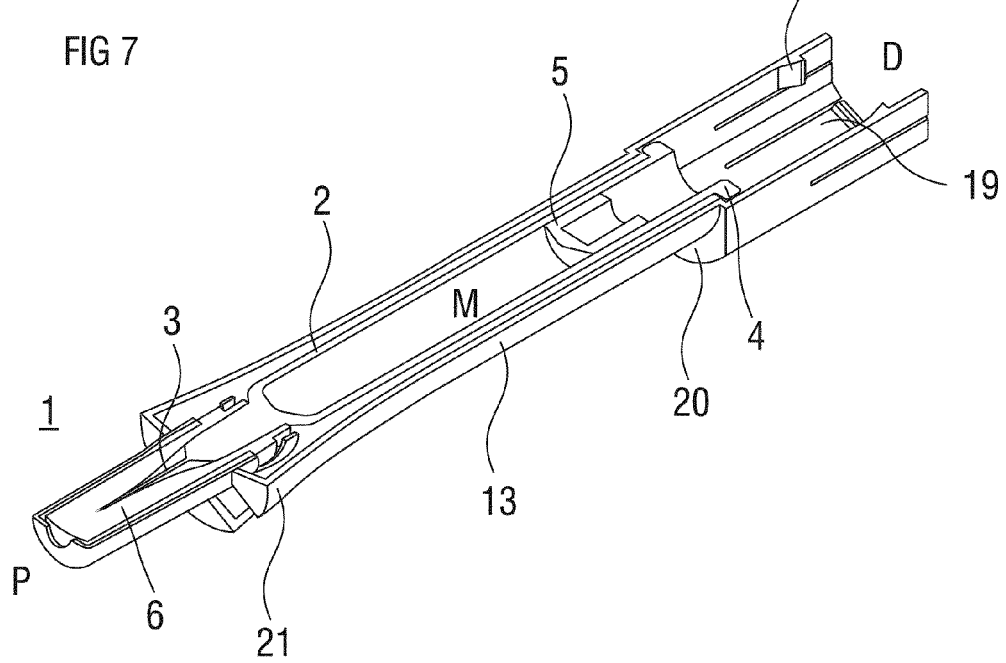
FIG. 8 is an isometric longitudinal section of the third embodiment in a different section plane in the situation as in FIG. 7.

FIG. 7 is an isometric longitudinal section of a third embodiment of the front end 1 prior to use. FIG. 8 is an isometric longitudinal section of the front end in a different section plane approximately 90° rotated relative to the section plane in FIG. 7 prior to use.

The front end 1 comprises a syringe 2 with an injection needle 3 attached to a proximal end of the syringe 2. At a distal end the syringe 2 comprises a finger flange 4. A stopper 5 is slidably arranged in the syringe 2 for distally sealing a cavity in the syringe 2 arranged to contain a liquid medicament M. The stopper 5 may be translated in a proximal direction P within the syringe 2 in order to displace the medicament M through the needle 3. A protective needle sheath 6 is removably arranged over the needle 3 for protecting the needle 3 from mechanical damage and for preventing finger access to the needle 3 thus reducing the risk of needle stick injuries.

The syringe 2 is arranged within an elongate housing 13.

The syringe 2 is assembled into the housing 13 through the distal end post both filling and application of the protective needle sheath 6. The syringe 2 may likewise be assembled into the housing 13 pre filling. During assembly the syringe 2 is translated in the proximal direction P until the finger flange 4 abuts against a second rib 20 in the housing 13. The syringe 2 is held in this position by friction between resilient compliant arms 21 on the proximal end of the housing 13 outwardly deflected by the protective needle sheath 6. The housing 13 may be locked to the syringe 2 in a proximal position by resilient first snaps 18 within the housing 13 latching to the syringe finger flange 4. The first snaps 18 exhibit a proximal ramp allowing the finger flange 4 to deflect the first snaps 18 outwards as the housing 13 is translated in the proximal direction P relative to the syringe 2. A distal side of the first snaps 18 is essentially perpendicular to a longitudinal axis of the front end 1 preventing the housing 13 from re-translating in the distal direction D as soon as the first snaps 18 flex inwards behind the finger flange 4. A pair of resilient second snaps 19 is arranged in the housing 13 in a manner to prevent the syringe 2 from being translated out of the distal end of the housing 13. The second snaps 19 are distally ramped to allow insertion of the syringe 2 into the housing 13 during assembly.

In order to prepare for an injection the front end 1 is connected to the re-usable back end (not illustrated).

The user then removes the protective needle sheath 6 from the front end 1. The compliant arms 21 on the housing 13 are thus allowed to relax and flex inwards for closing in around the tip of the needle 3. The syringe 2 is now free to move with respect to the housing 13.

During operation of the re-usable back end, the housing 13 can be moved as required.

Figure 9:
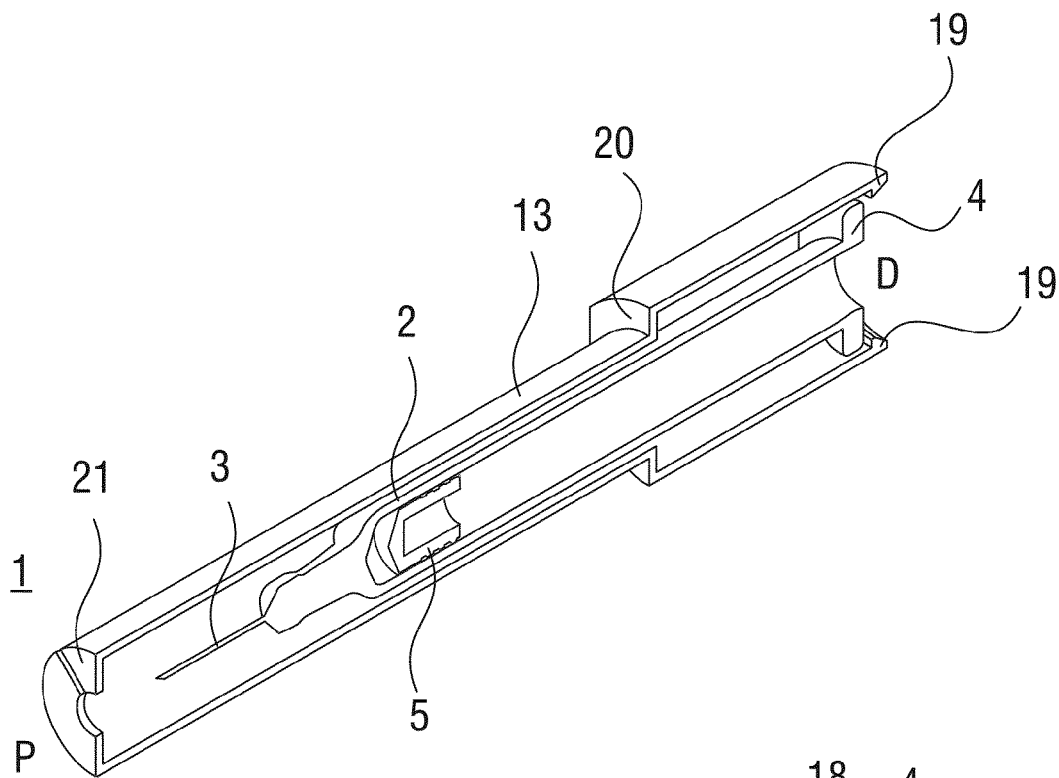
FIG. 9 is an isometric longitudinal section of the third embodiment post use in the section plane as in FIG. 7.
Figure 10:
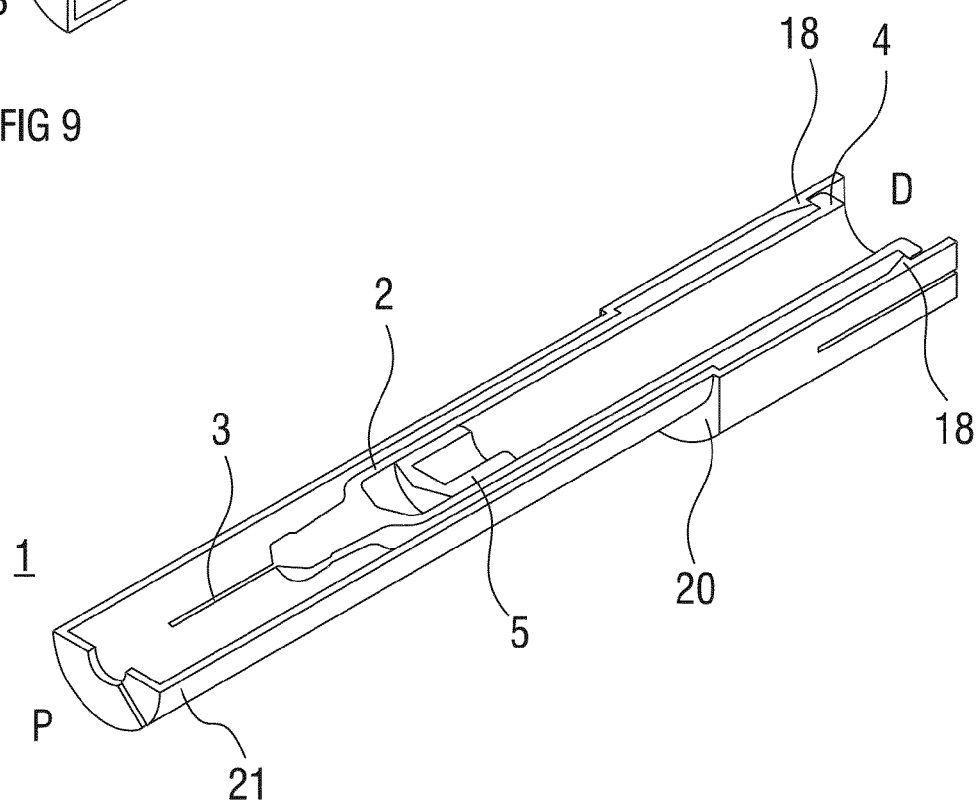
FIG. 10 is an isometric longitudinal section of the third embodiment in the section plane as in FIG. 8 in the situation as in FIG. 9.

The re-usable back end may be arranged to move the housing 13 in the proximal direction P relative to the syringe 2 at the end of injection. For this purpose means may be provided by which the re-usable back end may hold the syringe 2 to move it distally relative to the housing 13, e.g. a syringe carrier. A syringe return biasing the syringe 2 in the distal direction D relative to the housing 13 spring may likewise be provided. The housing 13 is locked in the proximal position by the first snaps 18 preventing access to the needle 3 (see FIGS. 9 and 10). The front end 1 may then be removed form the re-usable back end.

Figure 11:
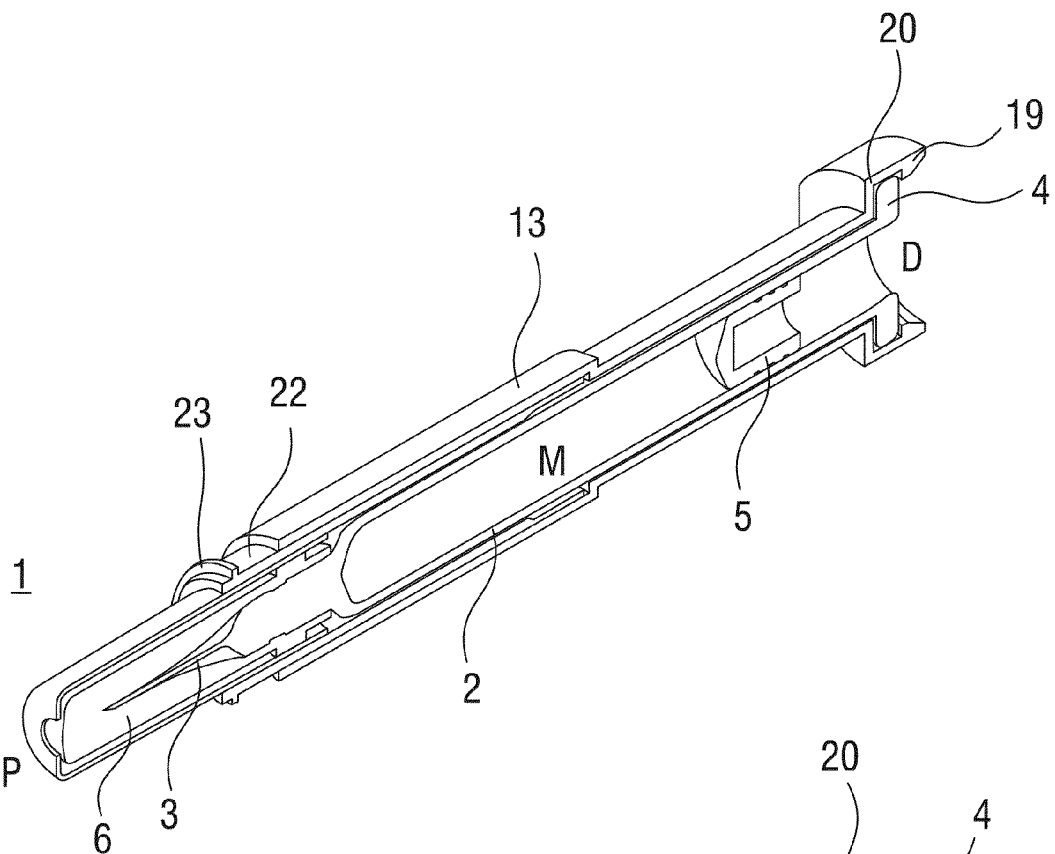
FIG. 11 is an isometric longitudinal section of a fourth embodiment prior to use.
Figure 12:
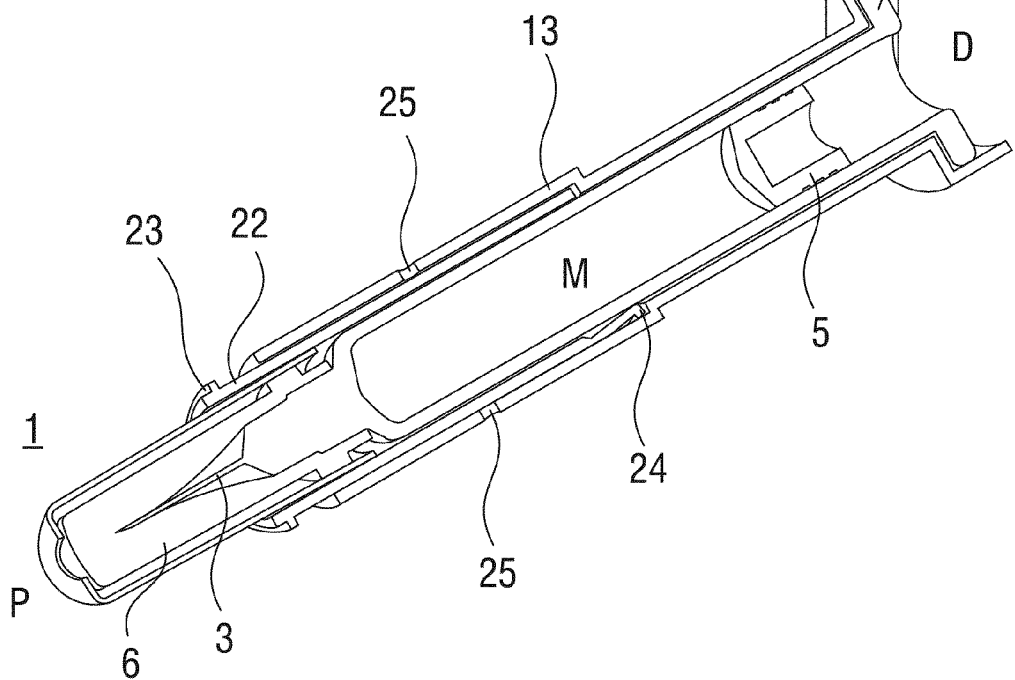
FIG. 12 is an isometric longitudinal section of the fourth embodiment prior to use in a different section plane.

FIG. 11 is an isometric longitudinal section of a fourth embodiment of the front end 1 prior to use. FIG. 12 is an isometric longitudinal section of the fourth embodiment prior to use in a different section plane approximately 45° rotated relative to the section plane in FIG. 11.

The front end 1 comprises a syringe 2 with an injection needle 3 attached to a proximal end of the syringe 2. At a distal end the syringe 2 comprises a finger flange 4. A stopper 5 is slidably arranged in the syringe 2 for distally sealing a cavity in the syringe 2 arranged to contain a liquid medicament M. The stopper 5 may be translated in a proximal direction P within the syringe 2 in order to displace the medicament M through the needle 3. A protective needle sheath 6 is removably arranged over the needle 3 for protecting the needle 3 from mechanical damage and for preventing finger access to the needle 3 thus reducing the risk of needle stick injuries.

The syringe 2 is arranged within an elongate housing 13. A sliding shroud 22 is telescoped in a proximal part of the housing 13. Prior to use the sliding shroud 22 is in a distal position. The protective needle sheath 6 is telescoped in the sliding shroud 22 and engaged to it by a friction fit.

The syringe 2 is assembled into the housing 13 through the distal end post both filling and application of the protective needle sheath 6. The syringe 2 may likewise be assembled into the housing 13 pre filling. During assembly the syringe 2 is translated in the proximal direction P until the finger flange 4 abuts against a second rib 20 in the housing 13. A pair of resilient second snaps 19 is arranged in the housing 13 for engaging the finger flange 4 in a manner to prevent the syringe 2 from being translated out of the distal end of the housing 13. The second snaps 19 are distally ramped to allow insertion of the syringe 2 into the housing 13 during assembly.

In order to prepare for an injection the front end 1 is loaded into the re-usable back end (not illustrated). The user removes the protective needle sheath 6 from the front end 1 by pulling it in the proximal direction P. As the user pulls the protective needle sheath 6 off the needle 3, the friction fit between the protective needle sheath 6 and the sliding shroud 22 causes the sliding shroud 22 to also be drawn in the proximal direction P and begin to obscure the needle 3. The re-usable back may be arranged to restrict the motion of the sliding shroud 22 by engaging a fourth shoulder 23 on the sliding shroud 22 such that the user can fully remove the protective needle sheath 6 from the needle 3 by overcoming the friction force between the protective needle sheath 6 and the sliding shroud 22. The sliding shroud 22 is now free to move with respect to the syringe 2.

During operation of the re-usable back end, the sliding shroud 22 can be moved as required by the reusable back-end.

At the end of the injection, the re-usable back end drives the sliding shroud 22 fully out in the proximal direction P in a manner to cover the needle 3 such that resilient second barbs 24 on the sliding shroud 22 engage into recesses 25 within the housing 13. This prevents access to the needle 3 once the front end 1 is removed from the reusable back end.

Figure 13:
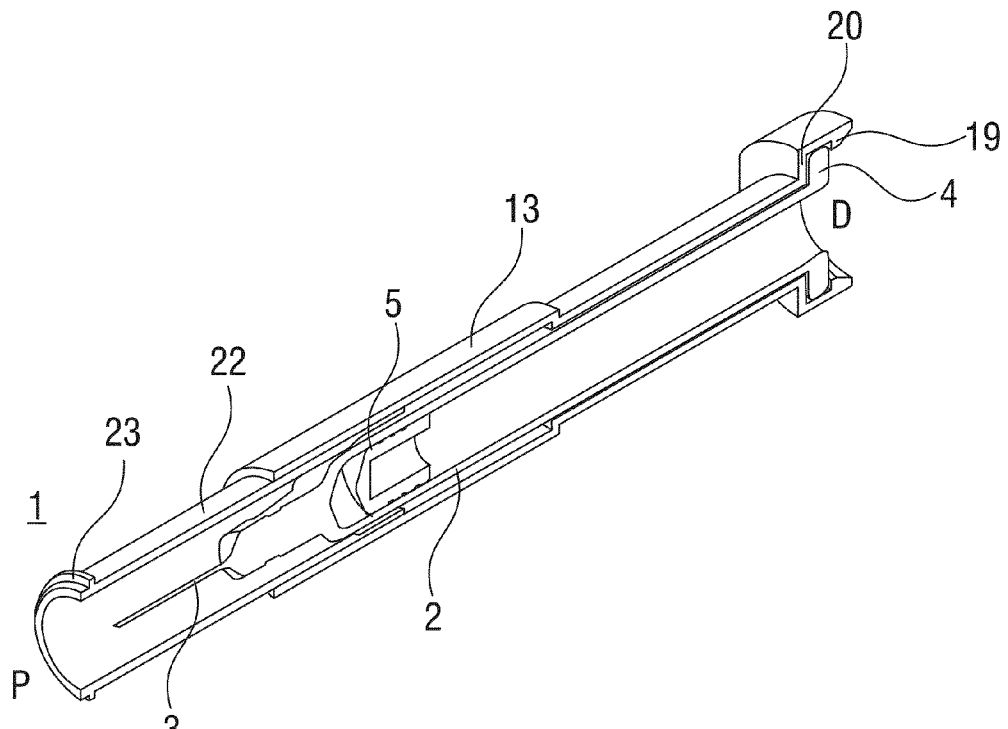
FIG. 13 is an isometric longitudinal section of the fourth embodiment post use in the section plane as in FIG. 11.
Figure 14:
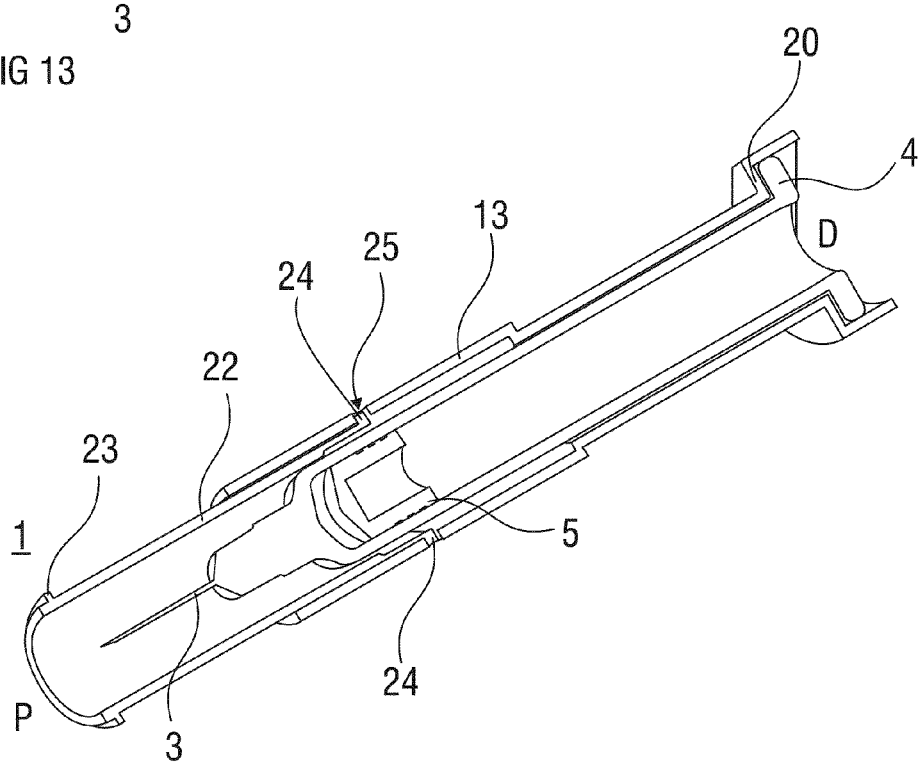
FIG. 14 is an isometric longitudinal section of the fourth embodiment post use in the section plane as in FIG. 12.

FIG. 13 is an isometric longitudinal section of the fourth embodiment of the front end 1 post use after removal from the re-usable back end in the section plane as in FIG. 11. FIG. 14 is an isometric longitudinal section of the fourth embodiment of the front end 1 post use in the section plane as in FIG. 12.

Figure 15:
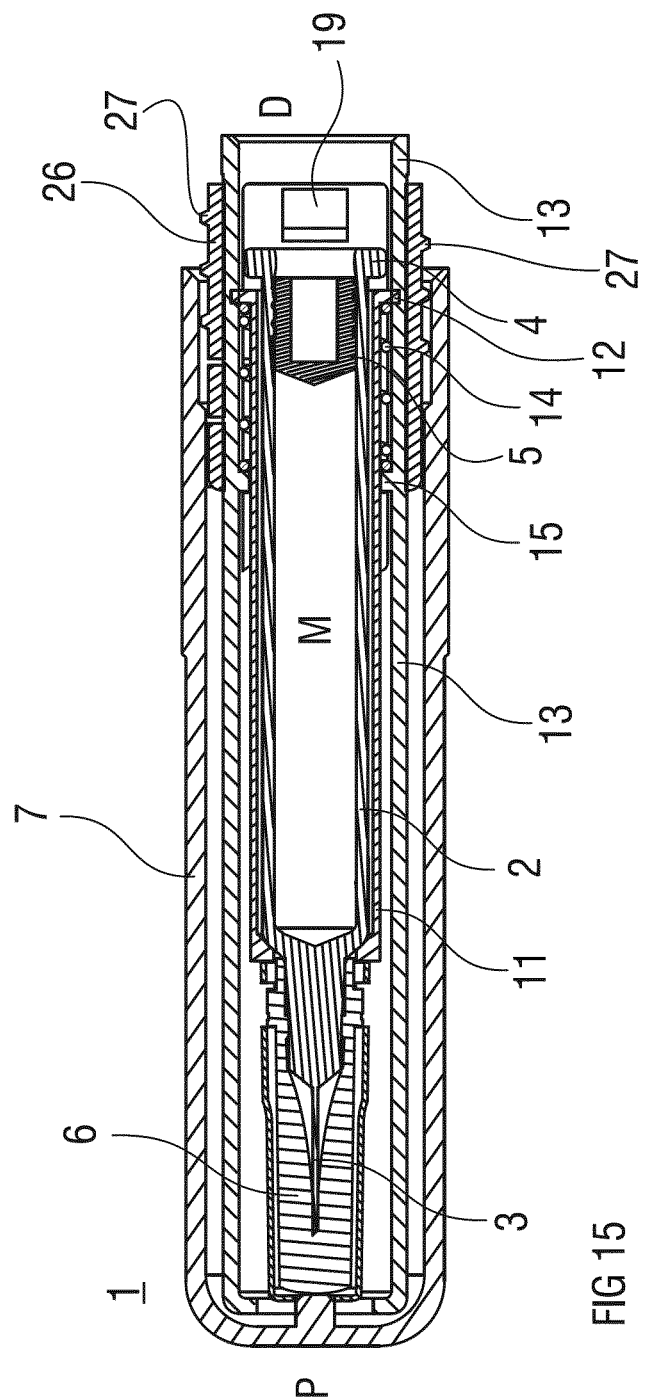
FIG. 15 is a longitudinal section of a fifth embodiment of a front end.
Figure 16:
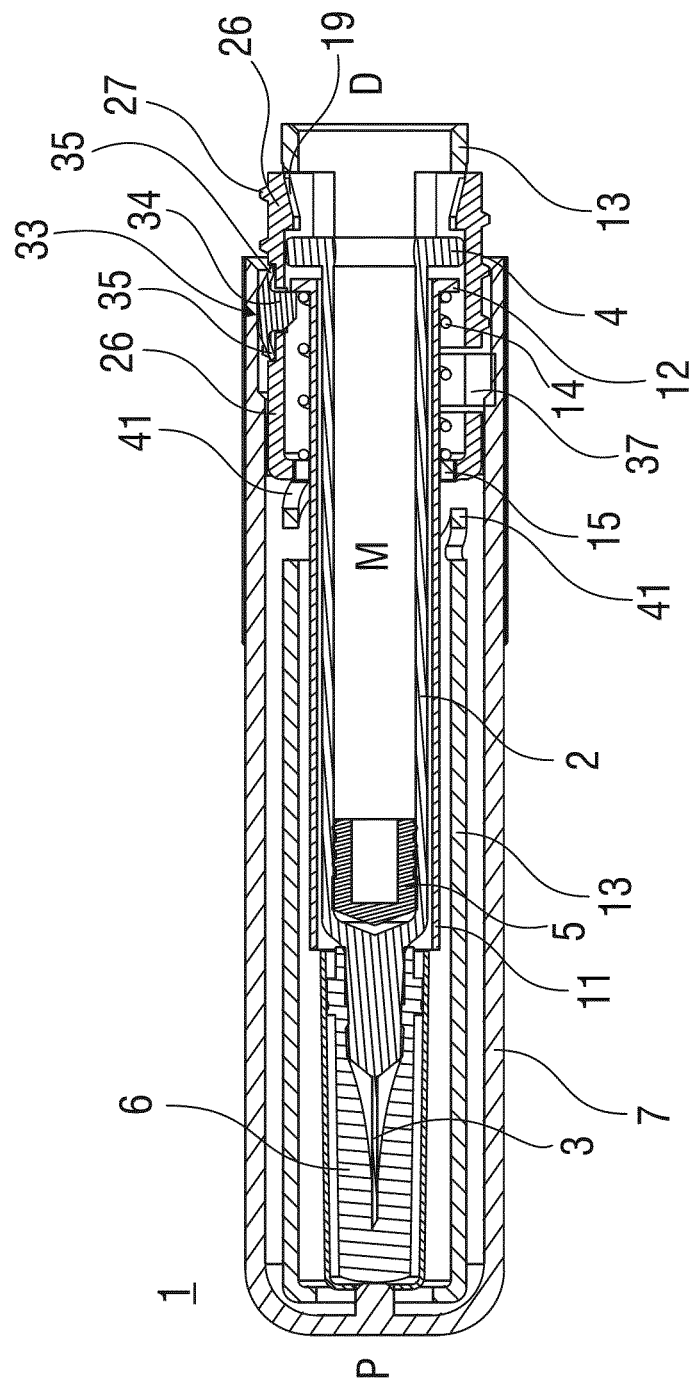
FIG. 16 is a longitudinal section of the fifth embodiment in a different section plane.

FIG. 15 is a longitudinal section of a fifth embodiment of a front end 1. FIG. 16 is a longitudinal section of the fifth embodiment in a different section plane.

The front end 1 comprises a syringe 2 with an injection needle 3 attached to a proximal end of the syringe 2. At a distal end the syringe 2 comprises a finger flange 4. A stopper 5 is slidably arranged in the syringe 2 for distally sealing a cavity in the syringe 2 arranged to contain a liquid medicament M. The stopper 5 may be translated in a proximal direction P within the syringe 2 in order to displace the medicament M through the needle 3. A protective needle sheath 6 is removably arranged over the needle 3 for protecting the needle 3 from mechanical damage and for preventing finger access to the needle 3 thus reducing the risk of needle stick injuries.

The syringe 2 is arranged within a syringe carrier 11 arranged to support the syringe 2 at its proximal end so as to couple the syringe 2 to the syringe carrier 11 for joint translation. The syringe carrier 11 is slidably arranged within an elongate housing 13. A syringe spring 14 in the shape of a compression spring is arranged between a second shoulder 12 on the distal end of the syringe carrier 11 and a third shoulder 15 in the housing 13 so as to bias the syringe carrier 11 in the distal direction D with respect to the housing 13.

The housing 13 is telescoped within a syringe retainer 26 at the distal end of the front end 1 arranged to be attached to a re-usable back end.

An outer sleeve 7 or cap is removably arranged over a substantial length of the housing 13 and the syringe retainer 26. The outer sleeve 7 is engaged to the protective needle sheath 6 for joint axial translation.

The syringe 2 is assembled into the housing 13 and syringe retainer 26 through the distal end post both filling and application of the protective needle sheath 6. The syringe 2 may likewise be assembled into the housing 13 pre filling. A pair of resilient second snaps 19 is arranged in the syringe retainer 26 for engaging the finger flange 4 in a manner to prevent the syringe 2 from being translated out of the distal end of the syringe retainer 26. The second snaps 19 are distally ramped to allow insertion of the syringe 2 into the syringe retainer 26 during assembly.

In order to prepare for an injection the user attaches the front end 1 to the re-usable back end using a screw thread 27 on the syringe retainer 26. The method of attachment is illustrated with a screw thread 27 by way of example however a snap, bayonet, or push fit could be used instead.

The user removes the outer sleeve 7 from the syringe retainer 26. The protective needle sheath 6 is attached to the outer sleeve 7 and therefore the protective needle sheath 6 is removed with the outer sleeve 7 or cap.

The protective needle sheath 6 may be attached to the outer sleeve 7 by one of the options illustrated in the FIGS. 23 to 28.

Figure 23:
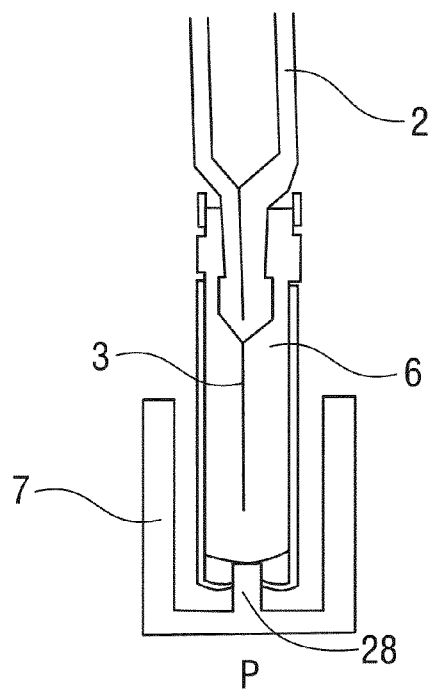
FIG. 23 is a longitudinal section of the protective needle sheath engaged to the cover.

FIG. 23 illustrates the outer sleeve 7 having an inward boss 28 attached through an opening in the proximal end of the protective needle sheath 6 by a push fit or bump or glued or ultrasonic welded inside the opening.

Figure 24:
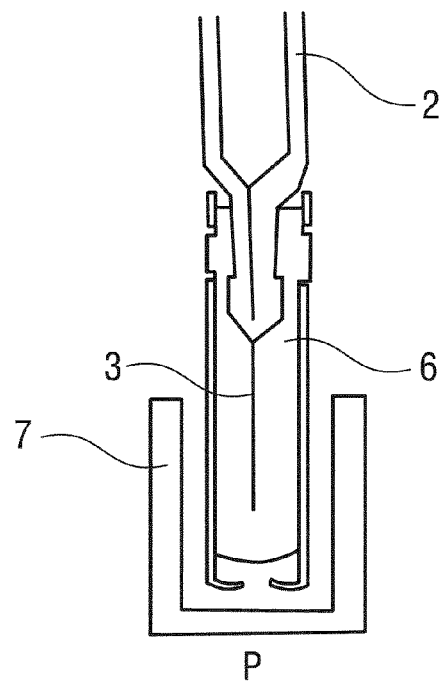
FIG. 24 is a longitudinal section of another embodiment of the engagement between the protective needle sheath and the cover.

FIG. 24 illustrates the outer sleeve 7 being push fitted over an external diameter of the protective needle sheath 6 or glued or ultrasonic welded to the external diameter.

Figure 25:
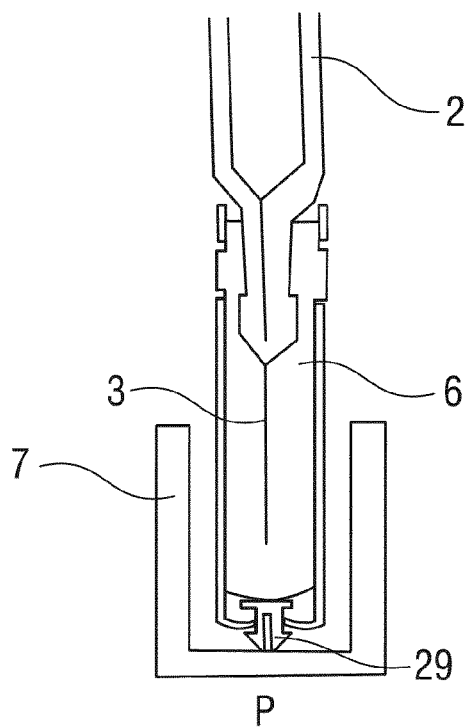
FIG. 25 is a longitudinal section of a third embodiment of the engagement between the protective needle sheath and the cover.

FIG. 25 illustrates the outer sleeve 7 and the protective needle sheath 6 being connected by an additional snap fit part 29 engaged in openings in both the protective needle sheath 6 and the outer sleeve 7.

Figure 26:
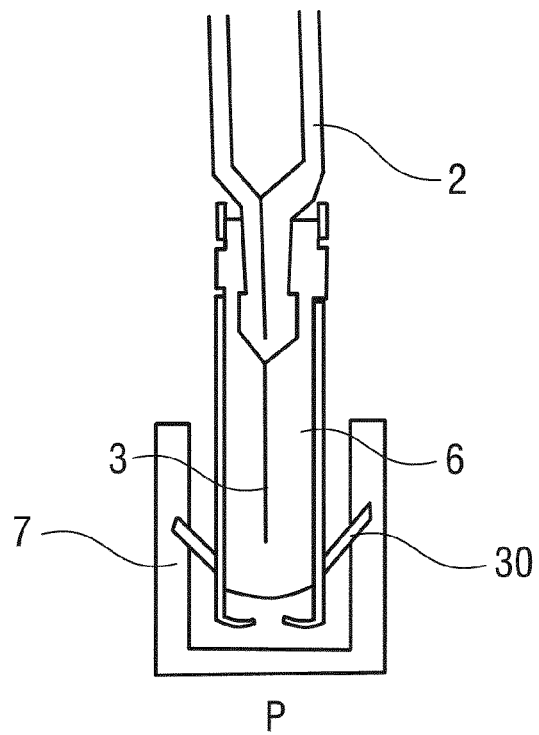
FIG. 26 is a longitudinal section of a fourth embodiment of the engagement between the protective needle sheath and the cover.

FIG. 26 illustrates the outer sleeve 7 and the protective needle sheath 6 being connected by a star washer 30 arranged over the external diameter of the protective needle sheath 6 and outwardly engaged to an internal diameter of the outer sleeve 7.

Figure 27:
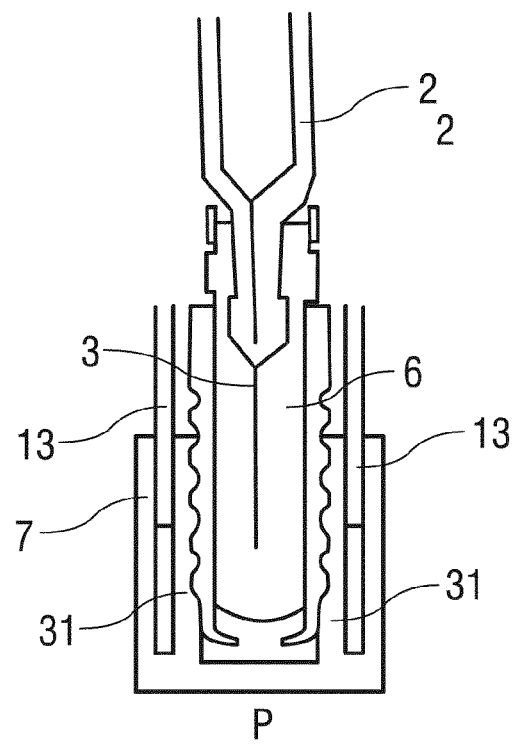
FIG. 27 is a longitudinal section of a fifth embodiment of the engagement between the protective needle sheath and the cover.

In FIG. 27 the protective needle sheath 6 has an external structure in the shape of a finger grip. The outer sleeve 7 or cap has at least two profiled arms 31 extending in the distal direction D from a proximal face of the outer sleeve 7. The profiles of the profiled arms 31 are engaged to the finger grip of the protective needle sheath 6. The profiled arms 31 are outwardly supported by the housing 13 telescoped inside the outer sleeve 7 such that the profiled arms 31 cannot flex outwards and disengage the protective needle sheath 6. As the outer sleeve 7 is being pulled off in the proximal direction P the protective needle sheath 6 is thus firmly held by the profiled arms 31. When the outer sleeve 7 is pulled to such an extent that the profiled arms 31 are no longer supported by the housing 13 the friction between the protective needle sheath 6 and a hub on the syringe 2 mounting the needle 3 has already been overcome.

Figure 28:
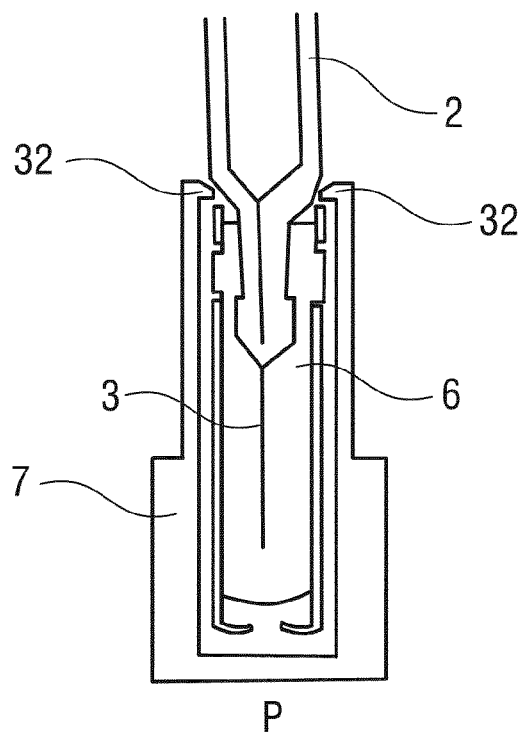
FIG. 28 is a longitudinal section of a sixth embodiment of the engagement between the protective needle sheath and the cover.

FIG. 28 illustrates the outer sleeve 7 having at least two distal snaps 32 engaged distally behind a distal edge of the protective needle sheath 6. The distal snaps 32 could likewise be engaged behind a shoulder on the protective needle sheath 6. Distal ramps on the distal snaps 32 are arranged to facilitate assembly of the outer sleeve 7 over the protective needle sheath 6.

As the outer sleeve 7 is removed, movement of the syringe 2 and compression of the syringe spring 14 is prevented by a syringe lock 33 to ensure the protective needle shield 6 is dislodged and ensure that the syringe 2 does not move in the proximal direction P.

The syringe lock 33 comprises a hub 34 extending through a lateral aperture in the syringe retainer 26 in a manner to engage the second shoulder 12 on the syringe carrier 11 to prevent to translation the syringe carrier 11 in the proximal direction P from the initial distal position shown in FIGS. 15 and 16. Two resilient arms 35 on the syringe lock 33 are arranged against an outer surface of the syringe retainer 26 in a manner to bias the hub 34 outwardly so as to disengage it from the second shoulder 12. However, in the initial state, the syringe lock 33 is outwardly supported by the outer sleeve 7 so as to prevent outward deflection of the hub 34 and hence disengagement of the syringe lock 33.

The syringe lock 33 locks the syringe 2 to the syringe retainer 26 when the outer sleeve 7 or cap is in place, thereby preventing syringe 2 being translated in the proximal direction under the load generated by removal of the needle shield 6. The syringe lock 33 is deactivated upon partial removal of the outer sleeve 7, at which position the load generated by removal of the needle shield has diminished, to enable the syringe 2 to be moved by a plunger of the re-usable back end (not illustrated).

Figure 20:
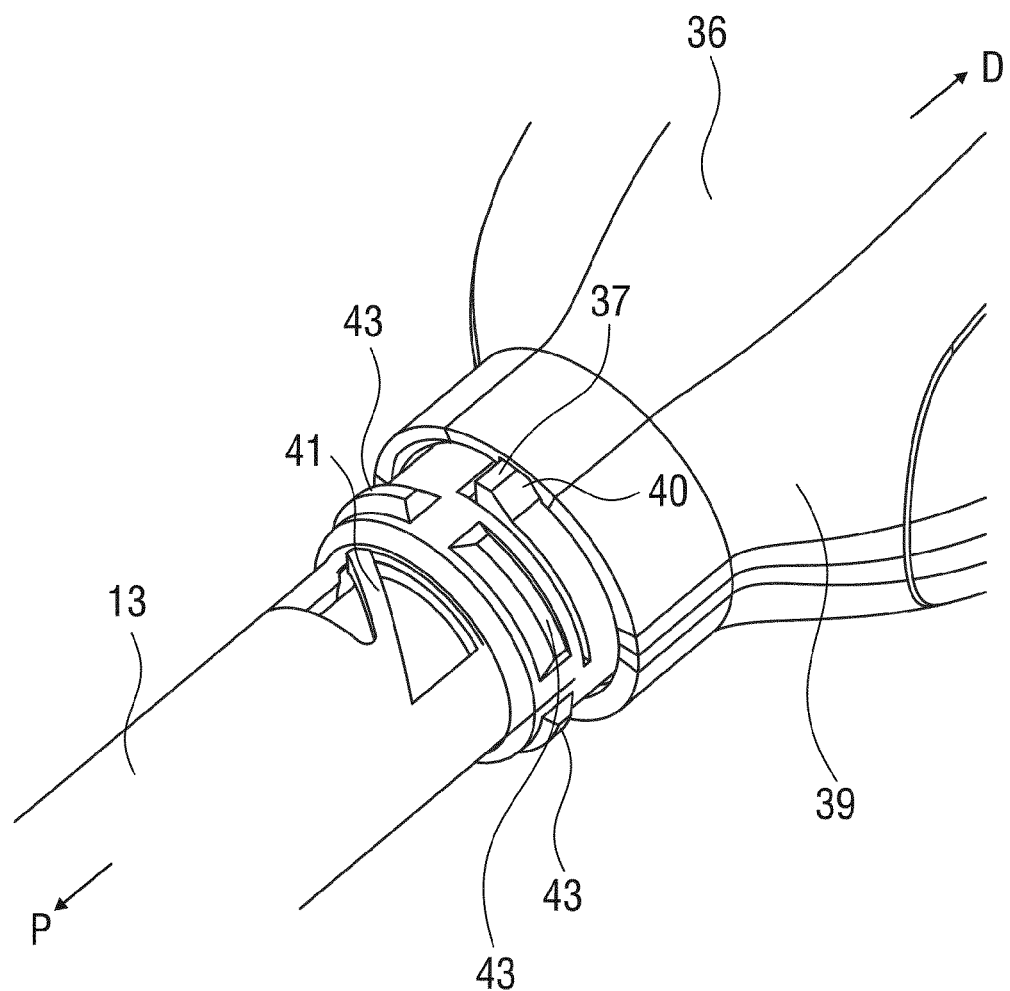
FIG. 20 is an isometric detail view of the fifth embodiment mounted to a re-usable back end.
Figure 21:
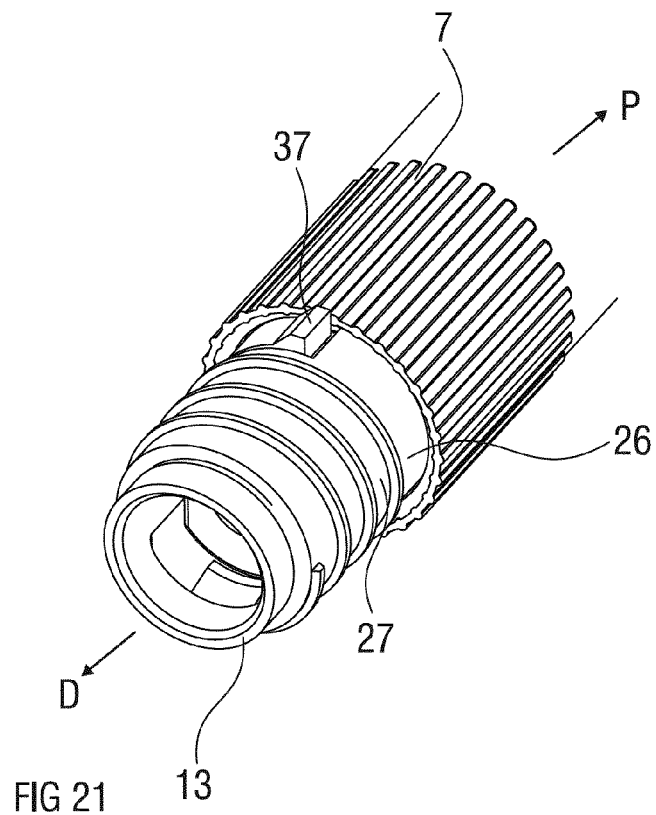
FIG. 21 is an isometric detail view of a distal end of the fifth embodiment.
Figure 22:
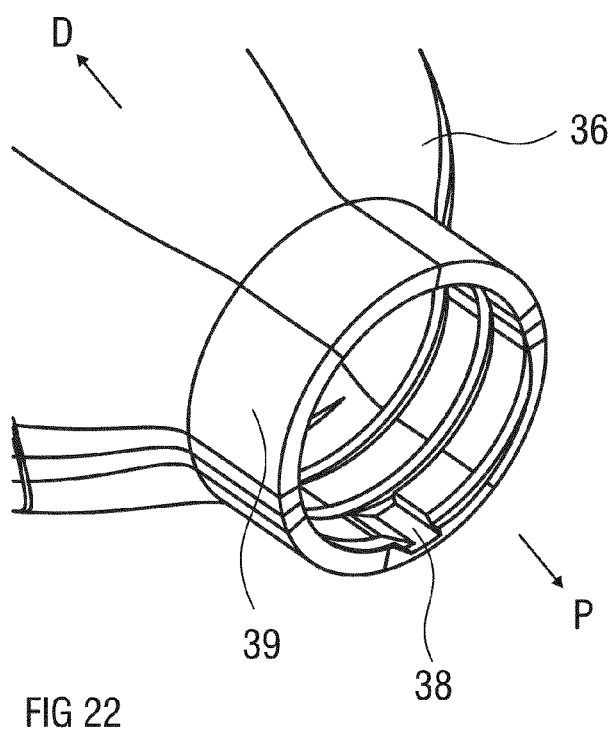
FIG. 22 is an isometric detail view of a proximal end of the re-usable back end.

FIG. 20 shows an isometric detail view of the front end 1 according to the fifth embodiment mounted to a re-usable back end 36. FIG. 21 shows the distal end of the front end 1 and FIG. 22 a proximal end of the re-usable back end 36 with an internally threaded mounting 39 for being connected to the front end 1. When the front end 1 is screwed into the mounting 39 as in FIG. 20 the outer sleeve 7 may be removed. A resilient locking barb 37 arranged proximally from the screw thread 27 on the syringe retainer 26 engages into an internal groove 38 within the internally threaded mounting 39 of the re-usable back end 36 and prevents rotation of the front end 1 thus preventing removal of the front end 1 from the re-usable back end 36 (see FIG. 20). A number of circumferential bumps 43 on the syringe retainer 26 are arranged proximally from the locking barb 37 to oppose removal of the outer sleeve 7 which may have a respective notch or shoulder for engaging the bumps 43 (not illustrated). Spaces on the perimeter of the syringe retainer 26 between the bumps 43 are arranged to receive drive dogs in the outer sleeve 7 in a manner to couple the outer sleeve 7 to the syringe retainer 26 for joint rotation when the outer sleeve 7 is applied to the syringe retainer 26.

The illustrated screw thread 27 is right-handed, hence the locking barb 37 and the internal groove 38 are arranged to prevent left-hand rotation. Screwing the front end 1 to the re-usable back end 36 is thought to be more intuitive with a right hand rotation. However, the required sense of rotation could be reversed by a left handed screw thread 27 and the locking barb 37 and internal groove 38 arranged to prevent right-hand rotation.

As the locking barb 37 partially remains proximally outside the mounting 39 it is inwardly deflected by the outer sleeve 7 prior to removal of the outer sleeve 7 and it can be re-deflected by the outer sleeve 7 being put back in place after injection so as to disengage the locking barb 37 from the internal groove 38 and allow removal of the front end 1 from the re-usable back end 36.

The front end 1 may be combined with the re-useable back end 36 pre or post removal of the protective needle sheath 6. As the front end 1 is rotated in a clockwise direction for attaching it to the re-usable back end 36 a chamfer 40 on the locking barb 37 ensures the locking barb 37 deflects inwardly upon contact with the re-usable back-end 36. Thus the function of the outer sleeve 7 in depressing the locking barb 37 can be dispensed with, i.e. the front end 1 may be assembled to the re-usable back end 36 with the outer sleeve 7 already removed.

When the user applies the proximal end of the auto-injector composed of the front end 1 and the re-usable back end to an injection site, e.g. a patient's skin, the housing 13 serving as a transfer sleeve is translated depressing an integrally moulded transfer spring 41 within the housing 13. The movement of the housing 13 can be detected in the re-usable back end 36 to ensure the auto-injector is only actuated when in contact with the injection site. The syringe spring 14 in the front end 1 permits movement of the syringe 2 under the driving force of the plunger of the re-usable back end 36. An injection depth is limited to the range of movement permitted by the syringe carrier 11 within the syringe retainer 26.

The load of the syringe spring 14 is resolved through a neck at the proximal end of the syringe 2 as opposed to the finger flange 4. This reduces the chance of damage to the syringe 2 during the injection process and also gives better injection depth control.

Figure 17:
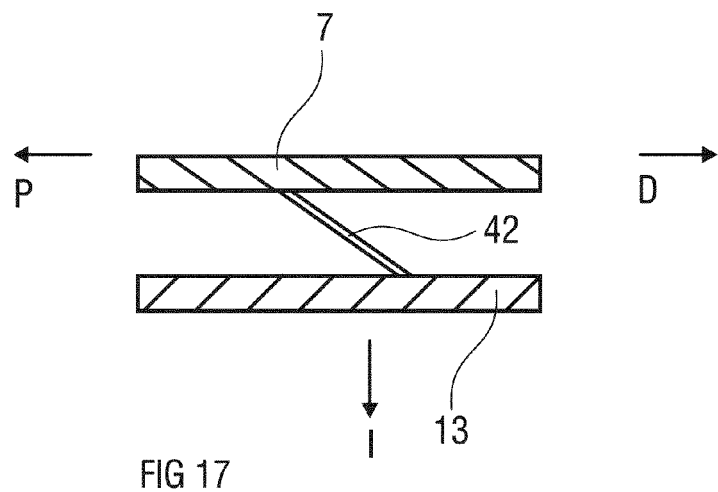
FIG. 17 is a schematic view of a cover retainer with a locking barb of the fifth embodiment.
Figure 18:
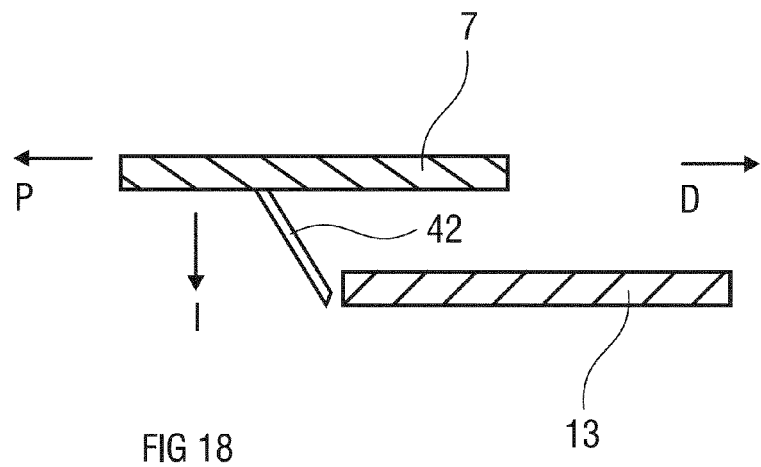
FIG. 18 is another schematic view of the cover retainer with the locking barb.
Figure 19:
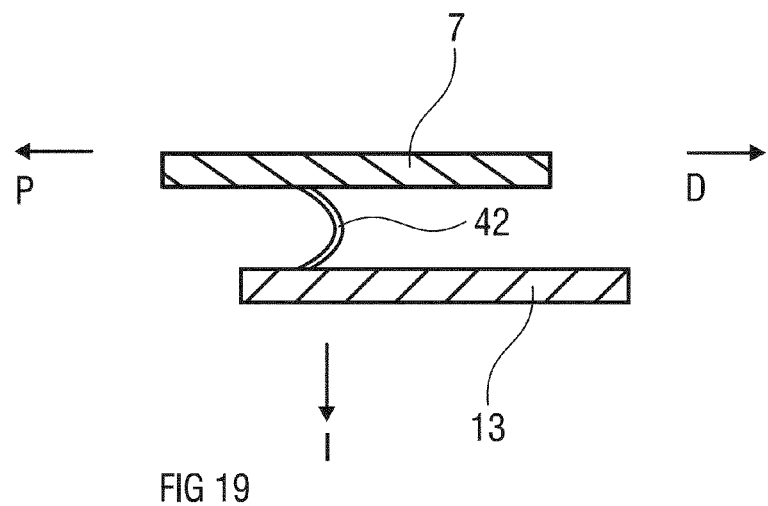
FIG. 19 is yet another schematic view of the cover retainer with the locking barb.

Once the injection has been completed, the user must reapply the outer sleeve 7 to the syringe retainer 26 in order to unscrew the front end 1 from the re-usable back end 36. As the outer sleeve 7 is reapplied, a cover retainer 42 in the shape of a metal clip attached to an inside of the outer sleeve 7 is deformed by contact to the housing 13 such that, once reapplied, the outer sleeve 7 cannot be removed. FIG. 17 illustrates the cover retainer 42 outwardly deflected by the housing 13 during removal of the outer sleeve 7, i.e. the outer sleeve 7 is moved in the proximal direction P relative to the housing 13. FIG. 18 shows the cover retainer 42 having travelled beyond the proximal end of the housing 13 thus deflecting in an inward direction I. FIG. 19 shows the outer sleeve 7 being reapplied over the housing 13. The cover retainer 42 hits the proximal end of the housing 13 and is bent on further distal motion of the outer sleeve 7 in a manner opposing removal of the outer sleeve 7 after reapplication.

The front end 1 according to the fifth embodiment ensures the access to the needle 3 is prevented once the protective needle sheath 6 is removed. This would reduce the chance of the user incurring an injury.

The options illustrated in the FIGS. 23 to 28 may likewise be combined with the first embodiment illustrated in FIGS. 1 and 2.

Once loaded into or attached to the re-usable back end 36, the syringe spring 14 of the front end 1 according to the second or fifth embodiment may be used to generate the force required to withdraw the needle 3 from the patient so this function does not have to be implemented in the re-usable back end 36 reducing the part count of the re-usable back end 36.

In the second, third and fifth embodiment of the front end the protective needle sheath may be removed before the front end 1 is combined with the re-usable back end 36. This may help to reduce the complexity and physical size of the assembled auto-injector.

The front end 1 according to the third, fourth and fifth embodiment prevents re-use of an emptied syringe 2 by enforcing the user to replace the protective needle sheath 6 post injection, and locking it in place. This reduces the health risk to the user of cross-contamination whether un-intended or through abuse of the front end 1.

The front end 1 according to either embodiment is preferably arranged as a packaged syringe 1 in the sense of a disposable device which is intended to be used once and to be disposed of after use thus reducing the risk of cross contamination between consecutive injections and eliminating the requirement for cleaning re-usable elements.

The front end 1 could also be arranged as a re-usable device, wherein the syringe 5 would be replaceably arranged in the front end 1 in such a manner that all components except the syringe 5 could be re-used.

The front end 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

The invention claimed is:

1. A front end for an auto-injector, the front end comprising: a syringe with an injection needle and a stopper, wherein the syringe is slidably arranged within a syringe retainer, wherein an outer sleeve for preventing access to the needle is removably arrangeable over the syringe retainer, wherein the syringe retainer comprises a screw thread for connecting it to a correspondent screw thread of a mounting of a re-usable auto-injector back end comprising a drive means for advancing the syringe and needle in a proximal direction for needle insertion and for advancing the stopper within the syringe for injection, wherein a resilient locking barb is arranged on the syringe retainer proximally from the screw thread of the syringe retainer, wherein the resilient locking barb is arranged to rotationally lock the syringe retainer to the mounting in an unscrewing direction when the front end is screwed to the re-usable back end and when the outer sleeve is removed, and the resilient locking barb exhibits a chamfer for inwardly deflecting the resilient locking barb by an internal surface of the mounting when rotated in a screwing direction, wherein the outer sleeve is arranged to unlock the resilient locking barb when arranged over the syringe retainer, the resilient locking barb being arranged to partially remain outside of the mounting so as to allow the outer sleeve to inwardly deflect the locking barb to unlock it, and wherein the resilient locking barb is arranged to engage an internal groove arranged in the mounting.

2. The front end according to claim 1, wherein the syringe is arranged within an elongate housing telescoped within the syringe retainer, wherein the housing is biased in the proximal direction and arranged to be translated in a distal direction when applied against an injection site, and wherein a distal end of the housing is arranged to protrude towards the re-usable back end to indicate its longitudinal position to the re-usable back end.

3. The front end according to claim 2, wherein the housing is arranged to protrude toward the re-usable back end to enable activation of a trigger mechanism of the re-usable back end, the trigger mechanism being coupled to the drive means such that the activation of the trigger mechanism enables release of the drive means for advancing the syringe and the needle and for advancing the stopper.

4. The front end according to claim 3, wherein the trigger mechanism comprises a trigger button coupled to the drive means such that manual actuation of the trigger button triggers the release of the drive means.

5. The front end according to claim 2, further comprising a cover retainer clip arranged in the outer sleeve extending distally and inwardly at an angle, wherein the cover retainer is inwardly biased so as to engage an outward surface of the housing in an initial state and during removal of the outer sleeve, wherein the cover retainer is arranged to deflect inwards when having travelled beyond a proximal end of the housing such that the cover retainer is deformed when the outer sleeve is reapplied to the housing in a manner opposing removal of the outer sleeve after reapplication.

6. The front end according to claim 2, further comprising at least one transfer spring arranged as a resilient part integrally moulded with the housing for biasing the housing in the proximal direction against the syringe retainer.

7. The front end according to claim 1, further comprising a protective needle sheath removably arrangeable over the needle, wherein the protective needle sheath is attached to the outer sleeve so as to be removed from the needle on removal of the outer sleeve from the syringe retainer.

8. The front end according to claim 7, wherein the outer sleeve is attached to the protective needle sheath by a push fit or bump or snap fit or glued or ultrasonic welded.

9. The front end according to claim 7, further comprising a star washer arranged over an external diameter of the protective needle sheath and outwardly engaged to an internal diameter of the outer sleeve.

10. The front end according to claim 7, wherein: the syringe is arranged within an elongate housing telescoped within the syringe retainer, wherein the housing is biased in the proximal direction and arranged to be translated in a distal direction when applied against an injection site, the protective needle sheath has an external profiled structure in the shape of a finger grip, wherein the outer sleeve has at least two profiled arms extending in the distal direction from a proximal end face of the outer sleeve, the profiled arms are engaged to the profiled structure of the protective needle sheath, and the housing is arranged to outwardly support the profiled arms when the outer sleeve is attached to the syringe retainer such that the profiled arms are prevented from deflecting outwards.

11. The front end according to claim 7, wherein the outer sleeve has at least one distal snap engaged distally behind a distal edge or shoulder of the protective needle sheath.

12. The front end according to claim 1, further comprising a syringe lock arranged for preventing translation of the syringe from a distal position in the proximal direction when the outer sleeve is arranged over the syringe retainer.

13. The front end according to claim 1, wherein the syringe is arranged in a syringe carrier arranged to support the syringe at its proximal end, the syringe carrier is tubular, and the syringe carrier is slidably arranged in the syringe retainer.

14. The front end according to claim 12, wherein: the syringe is arranged in a syringe carrier arranged to support the syringe at its proximal end, the syringe carrier is tubular, and the syringe carrier is slidably arranged in the syringe retainer, the syringe lock comprises a hub extending through a lateral aperture in the syringe retainer in a manner to engage a finger flange of the syringe or a second shoulder on a distal end of the syringe carrier, the hub is outwardly biased so as to disengage the finger flange or second shoulder, and the outer sleeve is arranged to outwardly support the hub so as to prevent outward deflection and disengagement of the syringe lock.

15. The front end according to claim 1, further comprising a syringe spring arranged to bias the syringe in a distal direction.

16. The front end according to claim 1, wherein the outer sleeve surrounds the syringe retainer when the outer sleeve is arranged over the syringe retainer.

17. The front end according to claim 1, wherein the outer sleeve is removed from the front end by being pulled in the proximal direction off the front end.

18. The front end according to claim 1, wherein, when the resilient locking barb is engaged to the internal groove, the internal groove prevents rotation of the syringe retainer relative to the mounting in the unscrewing direction.

19. The front end according to claim 1, wherein the syringe retainer comprises an engagement element positioned proximal from the resilient locking barb, the engagement element of the syringe retainer configured to engage an engagement element of the outer sleeve such that the syringe retainer and the outer sleeve jointly rotate when the outer sleeve is arranged over the syringe retainer.

20. The front end according to claim 1, wherein the drive means comprises a drive spring configured to engage the syringe and the stopper.

\* \* \* \* \*